(12) United States Patent  (10) Patent No.: US 7,744,614 B2
Gayheart et al.  (45) Date of Patent: Jun. 29, 2010

(54) CORNEAL EXCISION OR SCORING DEVICE

(75) Inventors: Robert A. Gayheart, Winchester, KY (US); Kanu M. Shukla, Lexington, KY (US); Archana K. Johnson, legal representative, Lexington, KY (US); Annette Carter, Frankfort, KY (US)

(73) Assignee: Krishna Imports, Incorporated, Lexington, KY (US)

( * ) Notice: Subject to any disclaimer, the term of this patent is extended or adjusted under 35 U.S.C. 154(b) by 177 days.

(21) Appl. No.: 11/452,017

(22) Filed: Jun. 13, 2006

(65) Prior Publication Data

US 2006/0287663 A1  Dec. 21, 2006

Related U.S. Application Data

(60) Provisional application No. 60/690,606, filed on Jun. 15, 2005, provisional application No. 60/761,177, filed on Jan. 23, 2006.

(51) Int. Cl.
 *A61F 9/00* (2006.01)
(52) U.S. Cl. ...................................... 606/166
(58) Field of Classification Search ................ 606/107, 606/161, 166, 167, 170–172, 179, 180, 184; 623/5.11–5.16
 See application file for complete search history.

(56) References Cited

U.S. PATENT DOCUMENTS

| 164,667 | A |   | 6/1875 | Winslow |
| 2,473,968 | A | * | 6/1949 | Paton .......................... 606/166 |
| 4,205,682 | A | * | 6/1980 | Crock et al. ................. 606/166 |
| 4,417,579 | A |   | 11/1983 | Soloviev et al. |
| 4,515,157 | A |   | 5/1985 | Fedorov et al. |
| 4,705,035 | A |   | 11/1987 | Givens |
| 4,739,761 | A |   | 4/1988 | Grandon |
| 4,844,060 | A |   | 7/1989 | Krumeich |
| 4,961,744 | A |   | 10/1990 | Kilmer et al. |
| 5,063,942 | A |   | 11/1991 | Kilmer et al. |
| 5,290,301 | A |   | 3/1994 | Lieberman |
| 5,346,497 | A |   | 9/1994 | Simon et al. |
| 5,486,188 | A |   | 1/1996 | Smith |
| 5,649,922 | A |   | 7/1997 | Yavitz |

(Continued)

FOREIGN PATENT DOCUMENTS

FR   2693368   1/1994

(Continued)

*Primary Examiner*—Todd E Manahan
*Assistant Examiner*—Jennifer L Hornberger
(74) *Attorney, Agent, or Firm*—King & Schickli, PLLC

(57) ABSTRACT

Disclosed is a corneal excision or scoring device. In one embodiment, the device includes a stabilizing portion having a first opening adapted to encircle an eye, such that at least a portion of the stabilizing portion engages the conjunctival fornix of the eye when inserted. The device may also include a second opening adapted to receive a cutting portion having a cutter capable of cutting or scoring the eye. In another embodiment, the device includes a stabilizing portion having an interior with a stop and an exterior serrated edge formed from a plurality of teeth. The stabilizing portion becomes inserted in an eye, such that the serrated edge rests on a sclera of the eye. Next, a cutting portion becomes inserted into the stabilizing portion to cut or score the eye, and the stop limits the distance the cutting portion may be inserted. Related methods are also disclosed.

20 Claims, 13 Drawing Sheets

U.S. PATENT DOCUMENTS

| | | | |
|---|---|---|---|
| 5,964,776 A | 10/1999 | Peyman | |
| 6,143,010 A * | 11/2000 | Silvestrini et al. | 606/166 |
| 6,458,141 B1 | 10/2002 | Peyman | |
| 6,582,445 B1 | 6/2003 | Koons | |
| 2002/0013579 A1 | 1/2002 | Silvestrini | |
| 2004/0225284 A1 * | 11/2004 | Webb et al. | 606/5 |

FOREIGN PATENT DOCUMENTS

| | | |
|---|---|---|
| GB | 2 242 835 | 10/1991 |
| SU | 1535-541 | 1/1990 |

* cited by examiner

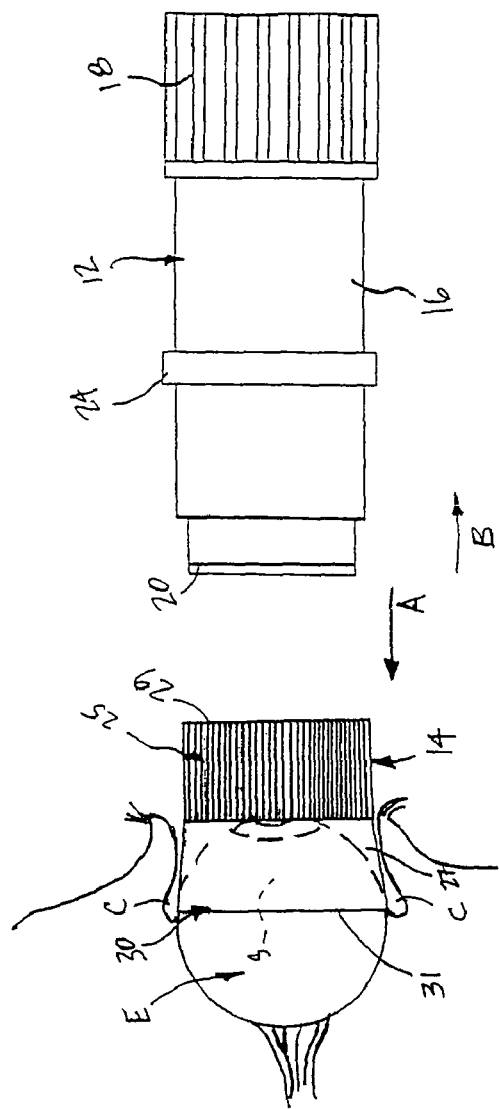
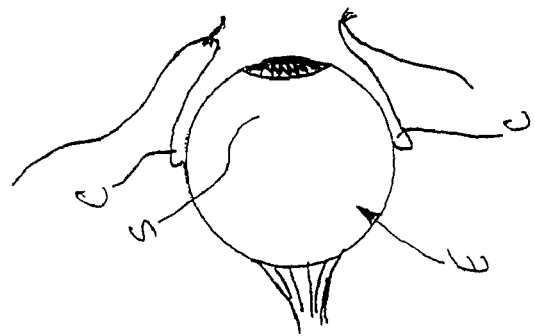
Fig. 4
Fig. 3

CORNEAL EXCISION OR SCORING DEVICE

This application claims the benefit of U.S. Provisional Application No. 60/690,606 filed Jun. 15, 2005 and U.S. Provisional Application No. 60/761,177 filed Jan. 23, 2006, the disclosures of which are incorporated herein by reference.

TECHNICAL FIELD

The present invention relates generally to the surgical arts and, more specifically, to a corneal excision or scoring device.

BACKGROUND OF THE INVENTION

In performing cornea surgery or transplants, such as keratolimbal allograft (KLAL), deep lamellar endothelial keratoplasty (DLEK), or penetrating keratoplasty (PKP), at least a portion of the cornea of the donor and the recipient is removed. Generally, a technician or other will use scissors, such as the commonly known castroviejo scissors, to obtain transplant material from a donor. Once the transplant material has been obtained, a surgeon will use a tool often referred to as a "trephine" to remove a damaged region of a recipient's eye and thus prepare an area to receive transplant material from the donor. The surgeon will use a similar trephine device to obtain a portion of the transplant material (sometimes referred to as a "button"). At this point, the surgeon may place the button into the receiving area of the recipient's eye. Once in place, the surgeon may use micro-sutures, biomedical adhesive material, or other means to hold the button.

Due to the delicate nature of the eye and the transplant procedure, the technician must use extreme care in order to obtain the proper amount of transplant material without damaging it. If too deep an incision is made, the vitreous humor may become ruptured, therein collapsing the eye and damaging the potential transplant material.

Previous devices, such as the castroviejo scissors mentioned above, require the technician to make multiple "freehand" cuts in the eye. This often results in uneven cuts and inconsistent amounts of transplant material. These devices do not include provisions for stability of the device, thus further contributing to the inconsistent amounts of transplant material obtained. Also, these devices fail to include reliable provisions for measuring or limiting the depth of the cut. This can result in cutting either too little or too much transplant material. If too little material is cut, the transplant procedure may be ineffective and the transplant material may be ruined. If too much material is cut, the vitreous humor may become ruptured and the transplant material may be damaged, as previously mentioned. The relative unprecise nature of these devices results in increased likelihood of damage to the transplant material and recipient.

Accordingly, the surgical arts have need for a corneal excision device that enables the user to obtain consistent amounts of material in a single cut of the eye. The device should also include provisions to ensure accurate cutting depth. Finally, if the eye socket is too small to place the entire device on the eye, the device should function to score the cutting area of the eye so that the technician, surgeon, or other can have a guide for using scissors or other traditional surgical tools to remove the transplant material.

SUMMARY OF THE INVENTION

In accordance with the purposes of the present invention as described herein, a new and improved corneal excision or scoring device is disclosed. One embodiment of the present invention includes a stabilizing portion having a first opening adapted to engage the conjunctival fornix of the eye when inserted in the eye, and a second opening adapted to receive a cutting portion having a cutter capable of cutting or scoring the eye.

The stabilizing portion is substantially hollow and the diameter of the first opening is greater than the diameter of the second opening. A flared region of the stabilizing portion may include the first opening. In one embodiment, the stabilizing portion and the cutting portion are substantially concentric tubes, and the cutter is a substantially circular blade having an uninterrupted edge. The tube of the cutting portion further includes a projection positioned between the cutter and a gripping portion, the projection limits the depth of the cutting or scoring when it engages at least a portion of the stabilizing portion. The projection may comprise a substantially circular rim having a diameter greater than a diameter of the substantially cylindrical tube. In one embodiment, the stabilizing portion includes a gripping portion at one end and a flared region at the other end, the flared region assisting a user in engaging the stabilizing portion with the conjunctival fornix.

In accordance with another aspect of the invention, the corneal excision or scoring device comprises a stabilizing portion having a surface, the stabilizing portion becoming inserted in the eye to manipulate the position of the eye; and a cutting portion having a substantially uninterrupted sidewall positioned between a cutter and a projection positioned on an exterior of the sidewall, the cutting portion becoming inserted into the stabilizing portion to cut or score the eye. Engagement of the projection with the surface of the stabilizing portion functions to limit the distance the cutting portion may be inserted into the stabilizing portion. In one embodiment, the stabilizing portion and the cutting portion are substantially hollow concentric tubes. Also, the stabilizing portion may have a first opening adapted to encircle an eye, such that at least a portion of the stabilizing portion engages the conjunctival fornix of the eye when inserted in the eye.

In this configuration, the stabilizing portion also has a second opening adapted to receive the cutting portion, the diameter of the first opening being greater than the diameter of the second opening. Also, the projection may comprise a substantially circular rim having a diameter greater than a diameter of the substantially hollow tube of the cutting portion.

In another aspect of the invention, the corneal excision or scoring device comprises a cutting portion having a cutter and a projection spaced apart from the cutter; and a stabilizing portion having an interior with a stop and a serrated edge formed from a plurality of teeth. The stabilizing portion may become inserted in an eye, such that the serrated edge rests on a sclera of the eye, the cutting portion then becomes inserted into the stabilizing portion to cut or score the eye, and the stop limits the distance the cutting portion may be inserted.

The stabilizing portion and the cutting portion may comprise substantially hollow concentric tubes. Also, the projection may comprise a substantially circular rim having a diameter greater than a diameter of the substantially hollow tube of the cutting portion. In one embodiment, the stop comprises a projection, while in another embodiment, it comprises a recess. The cutting portion and stabilizing portion may each have matching threads, thereby enabling a user to mechanically join the cutting and stabilizing portions. In one embodiment, the substantially circular rim resides between the threads on the cutting portion and a gripping portion.

In accordance with another aspect of the invention, a method of corneal excision or scoring is disclosed. The method comprises engaging the conjunctival fornix of the eye and cutting or scoring the eye. The engaging step may comprise encircling the eye. In one embodiment, the engaging step comprises inserting a stabilizing portion of a corneal excision or scoring device into the eye, such that a portion of the stabilizing portion engages the conjunctival fornix of the eye. The cutting or scoring may comprise inserting a cutting portion into the stabilizing portion to cut or score the eye.

In another embodiment, the method comprises aligning a stabilizing portion of a corneal excision or scoring device on an eye; inserting the stabilizing portion into the eye, such that a portion of the stabilizing portion encircles the eye and engages the conjunctival fornix of the eye; manipulating the eye to a desired position; and inserting a cutting portion into the stabilizing portion to cut or score the eye. The step of inserting the cutting portion may comprise inserting until a projection engages a stop. The inserting the cutting portion step may also comprise inserting the cutting portion to cut or score an area 2-4 mm away from a limbus of the eye. The inserting the stabilizing portion may comprise inserting a stabilizing portion having an opening positioned in a flared region.

In the following description there is shown and described one possible embodiment of this invention, simply by way of illustration of one of the modes best suited to carry out the invention. As it will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIG. 3 is a representative partial cutaway side view of an eye;

FIG. 4 is a side view showing one method of use of the device of FIG. 1;

DETAILED DESCRIPTION OF THE INVENTION

Figure 1:
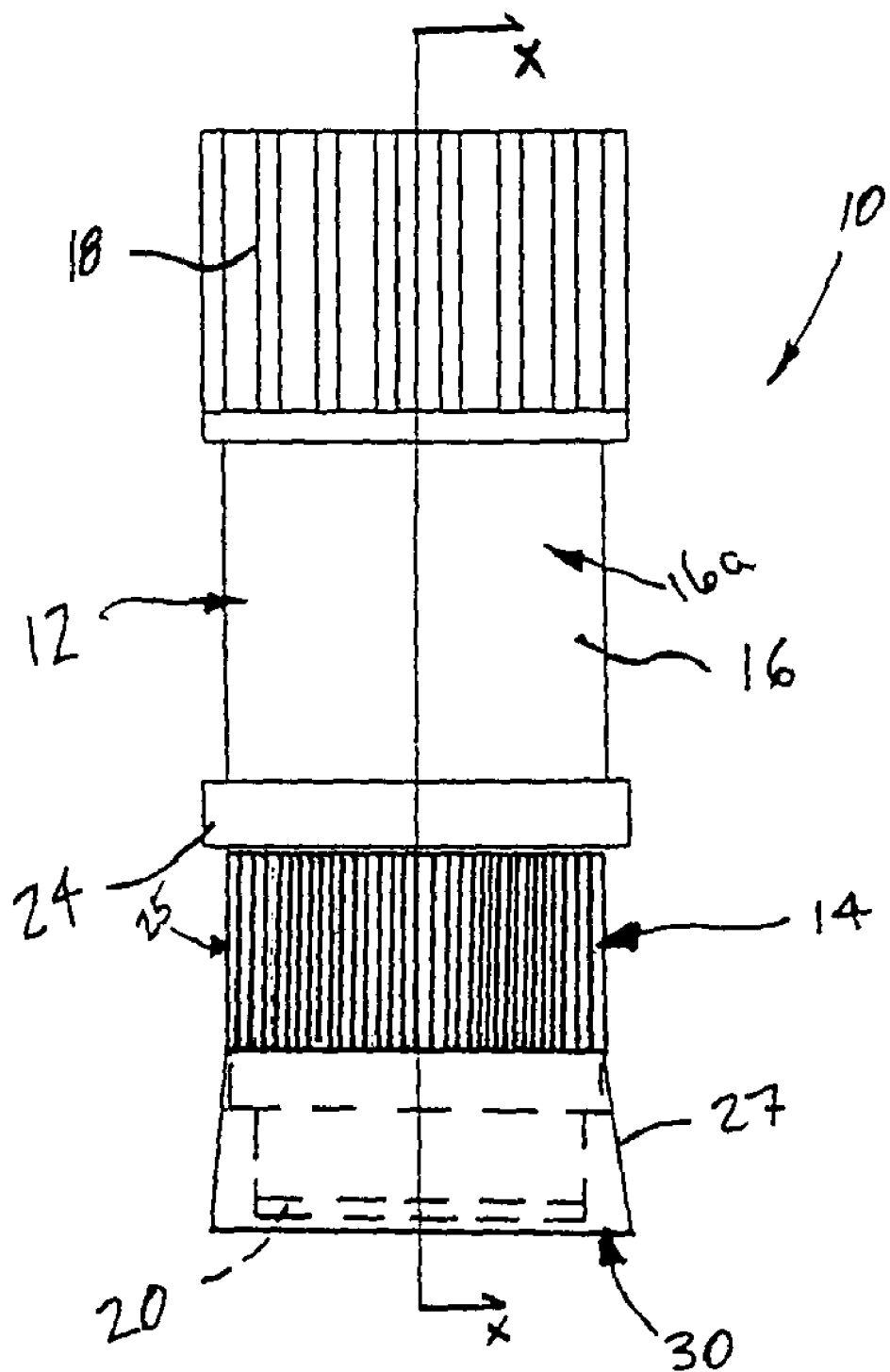
FIG. 1 is a side view of a corneal excision or scoring device forming one possible embodiment of the present invention.
Figure 2:
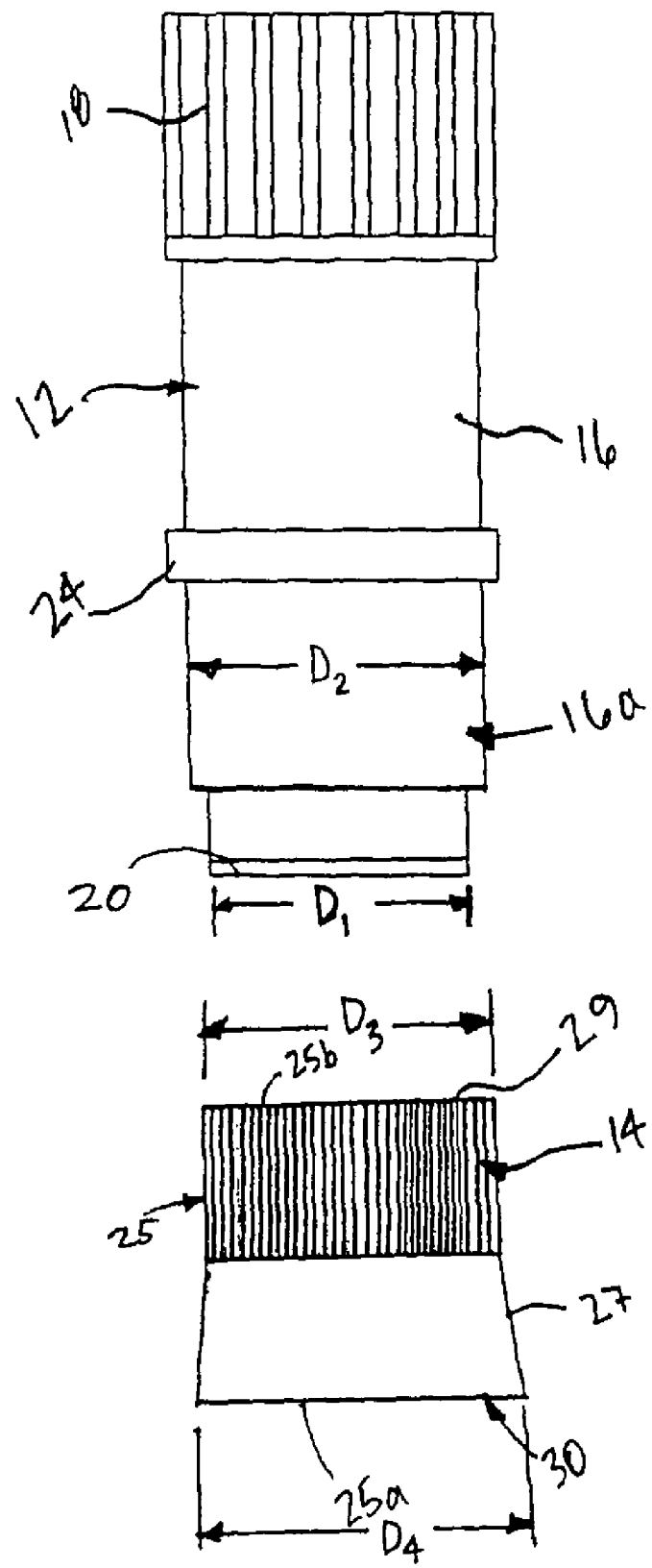
FIG. 2 is an exploded side view of the device of FIG. 1.

FIGS. 1-2, 4-6, illustrate one embodiment of the corneal excision or scoring device 10 of the present invention. With particular reference to FIGS. 1 and 2, the device 10 includes a cutting portion 12 and a stabilizing portion 14.

The cutting portion 12 comprises a substantially cylindrical tube 16 having a gripping portion 18 at one end and a cutter 20 at the other. The gripping portion 18 may include a plurality of knurls for assisting the user in manipulating the device. In one embodiment, the cutter 20 may take the form of an uninterrupted surgical blade substantially following the perimeter of the tube 16. The cutter 20 may be formed as one piece with the tube 16 or it may be attached to the tube 16 after forming via friction fit, brazing, welding or otherwise. Also, the cutter 20 may have any diameter, but preferably has a diameter $D_1$ (FIG. 2) between 15-19 mm. This enables the user to cut or score an area 2-4 mm away from a limbus L of the eye, thereby creating a substantially uniform rim of sclera material around a cornea. However, different dimensions of the cutter 20 enable the device 10 to be used with different size eye/eye sockets.

The cutting portion 12 may be formed from any material. In one embodiment, the tube 16 and gripping portion 18 are formed from a transparent or semi-transparent polymer material. Such a material provides the user of the cutting portion 12 with the maximum visibility of the eye when operating the device 10. Preferably the cutter 20 is formed from a surgical grade metal.

In one embodiment, the tube 16 has a substantially uninterrupted sidewall creating a smooth outer surface 16a so that the cutting portion 12 may become inserted into the stabilizing portion 14, as discussed below in further detail. Accordingly, the tube 16 preferably has a diameter $D_2$ less than a diameter $D_3$ of an opening 25b of a substantially cylindrical region or tube 25 of the stabilizing portion 14. One will appreciate the tube 16 and the tube 25 are substantially concentric when the cutting portion 12 is inserted into the stabilizing portion 14. The cutting portion 12 also includes a projection, such as a circular rim 24, positioned between the cutter 20 and gripping portion 18. Preferably the rim 24 has an outer diameter slightly larger than the diameter $D_2$ of the tube 16 and the tube 25 of the stabilizing portion 14. As discussed below, the rim 24 engages a surface, such as the top surface 29, of the stabilizing portion 14, therein functioning as a stop to the limit the distance the cutter 20 may be inserted into the eye. Accordingly, the rim 24 may be positioned at any point along the tube 16 depending on the depth of cut desired.

Figure 6:
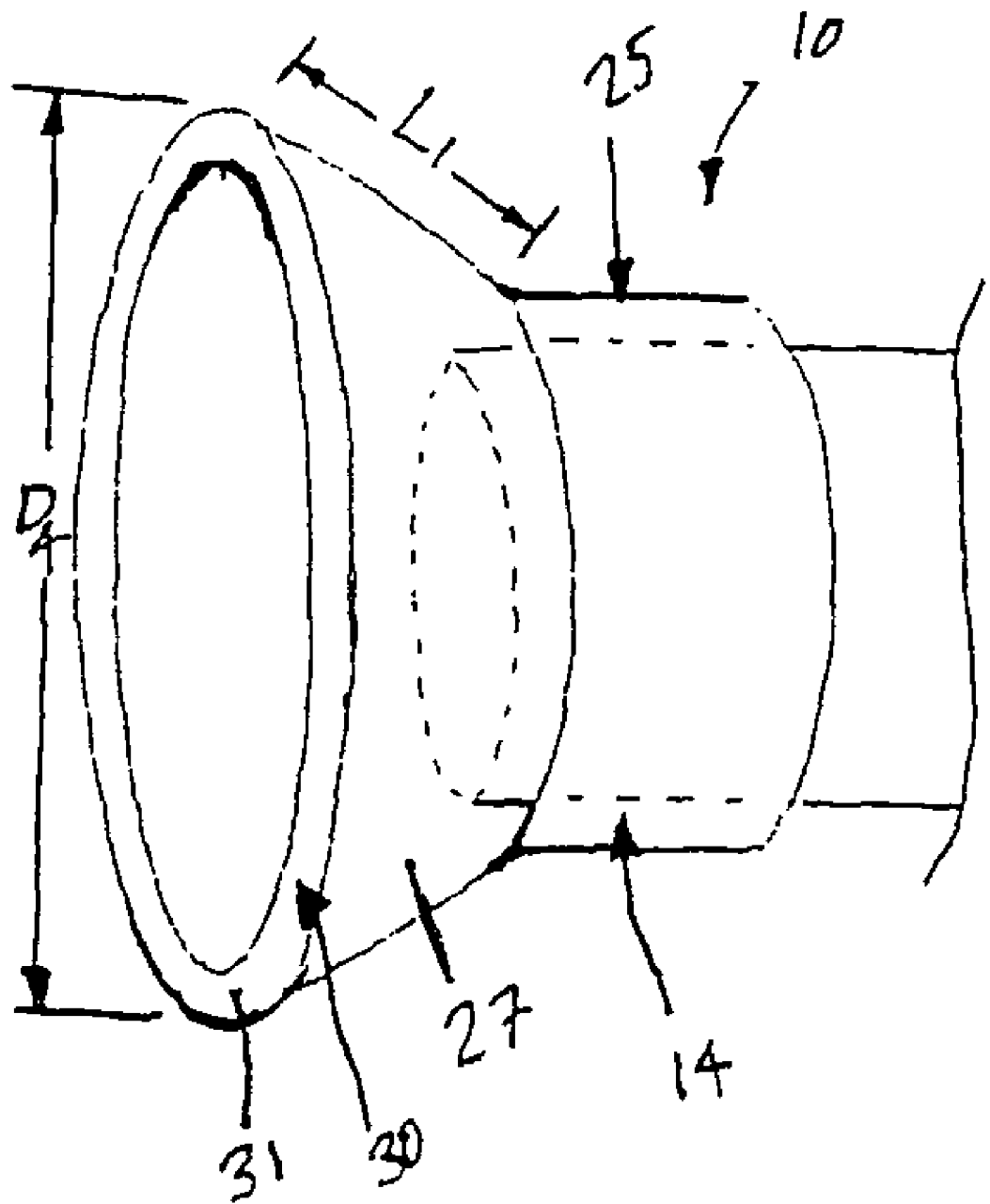
FIG. 6 is a partial perspective view of one embodiment of a stabilizing portion.
Figure 7:
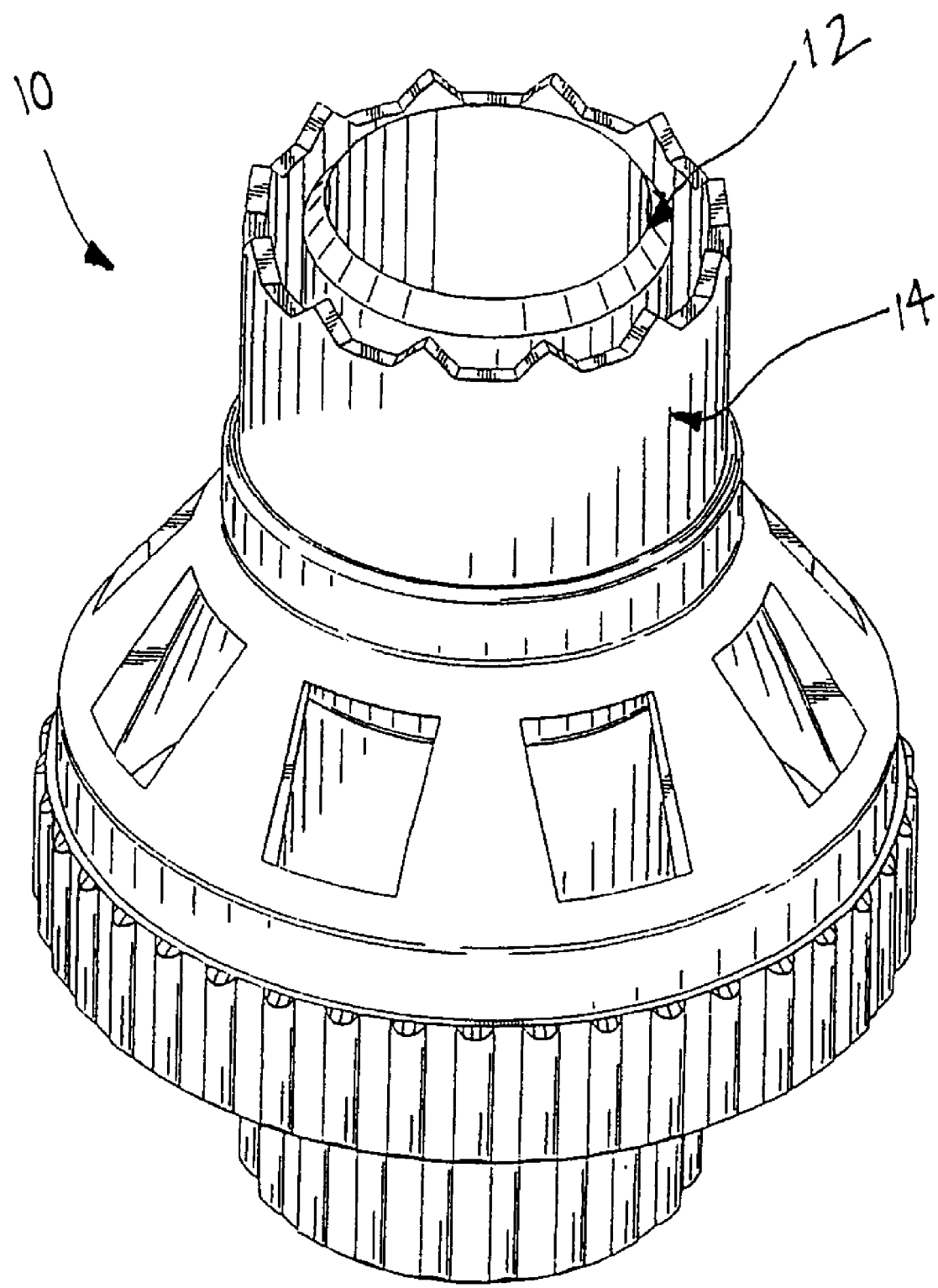
FIG. 7 is a perspective view of a second embodiment of a corneal excision or scoring device of the present invention.

With specific reference to FIGS. 2 and 6, the stabilizing portion 14 includes the tube 25 having the first opening 25a, a second opening 25b, a second gripping portion 28 at one end of the tube 25, and a flared region 27 having a stabilizer 30 at the other end. As shown, the stabilizer 30 comprises a substantially smooth or rounded edge 31 positioned at the end of the flared region 27. However, this edge 31 may be serrated, as discussed below. As shown, the diameter $D_4$ of the first opening 25a is greater than the diameter $D_3$ of the second opening 25b. In one embodiment, the diameter $D_4$ is approximately 24 mm, while the length $L_1$ of a wall 33 of the flared region 27 is approximately 10 mm (FIG. 6). These dimensions are preferable when a portion of the stabilizer 30 will contact the conjunctival fornix, as discussed below in further detail. However, $D_4$ and $L_1$ may be any dimension. Similar to the first gripping portion 18 on the cutting portion 12, the second gripping portion 28 may include a plurality of knurls positioned about the circumference of the tube 25.

Figure 14:
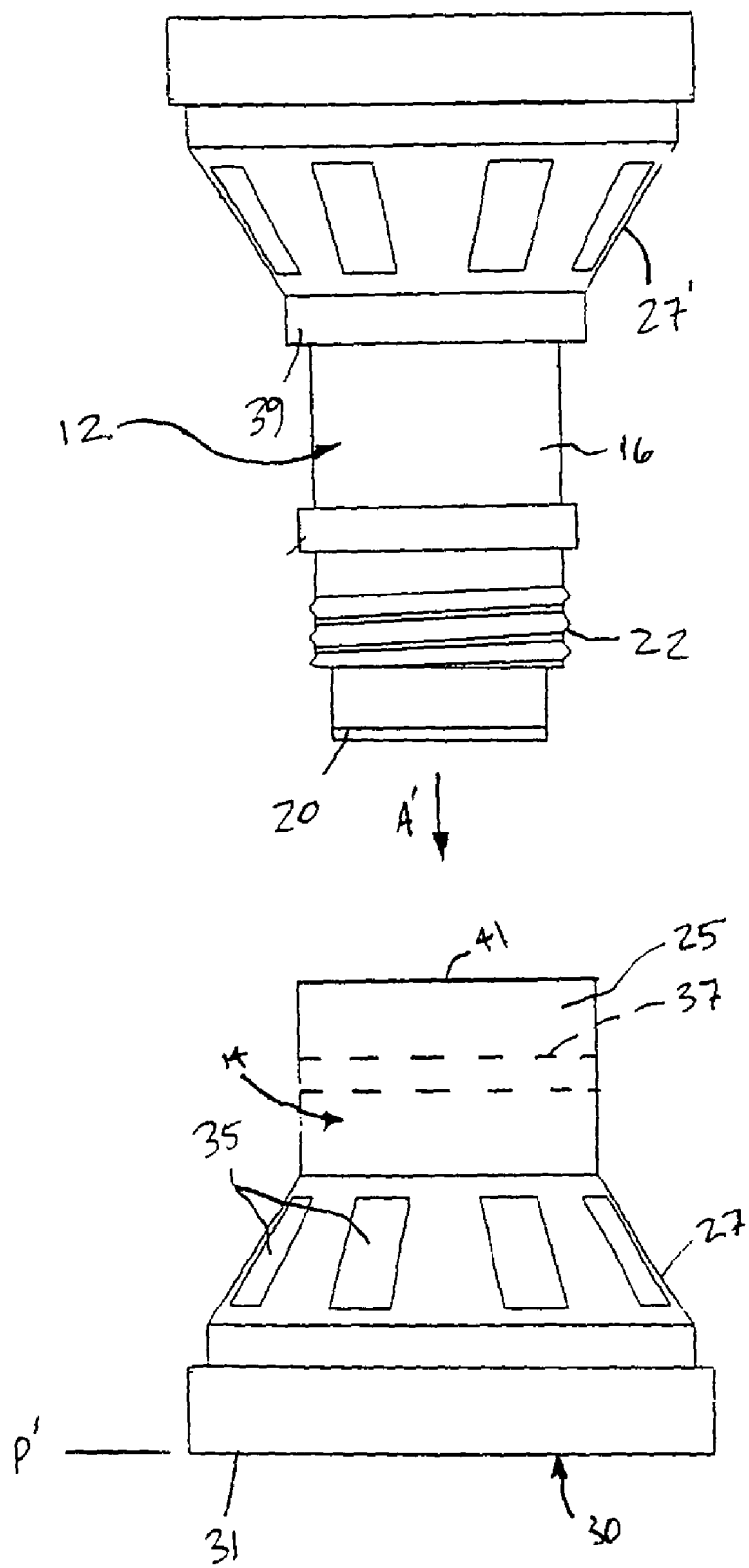
FIG. 14 is an exploded side view of a corneal excision or scoring device forming a third possible embodiment of the present invention.

As shown in FIG. 14, the flared region 27 may include a plurality of apertures 35. These apertures enable a user to better visualize the alignment of the corneal excision or scoring device 10 with the eye E. Alternatively, the flared region 27 may be substantially solid, as shown in FIGS. 1, 2, 4, and 6. Similar to the cutting portion 12, the stabilizing portion 14 may be formed of any material, but would preferably be a transparent or semi-transparent polymer. Again, this type of material provides the user with the greatest visibility of the eye E when operating the device 10.

A description of the assembly and method of use of the device 10 is now provided. To use the device 10, a user first aligns the stabilizing portion 14 on the eye and inserts it into the eye socket (FIG. 4). Given the appropriate diameter $D_4$ and the flared region 27, the stabilizing portion 14 encircles a portion of the eye E and may engage the conjunctival fornix C (FIGS. 3 and 4). One will appreciate that at least a portion of the stabilizing portion 14 touches the sclera S of the eye E. Accordingly, the stabilizing portion 14 functions to secure the eye E in place for cutting. It also enables a user to manipulate the eye to a desired position before cutting or scoring the eye.

Figure 5:
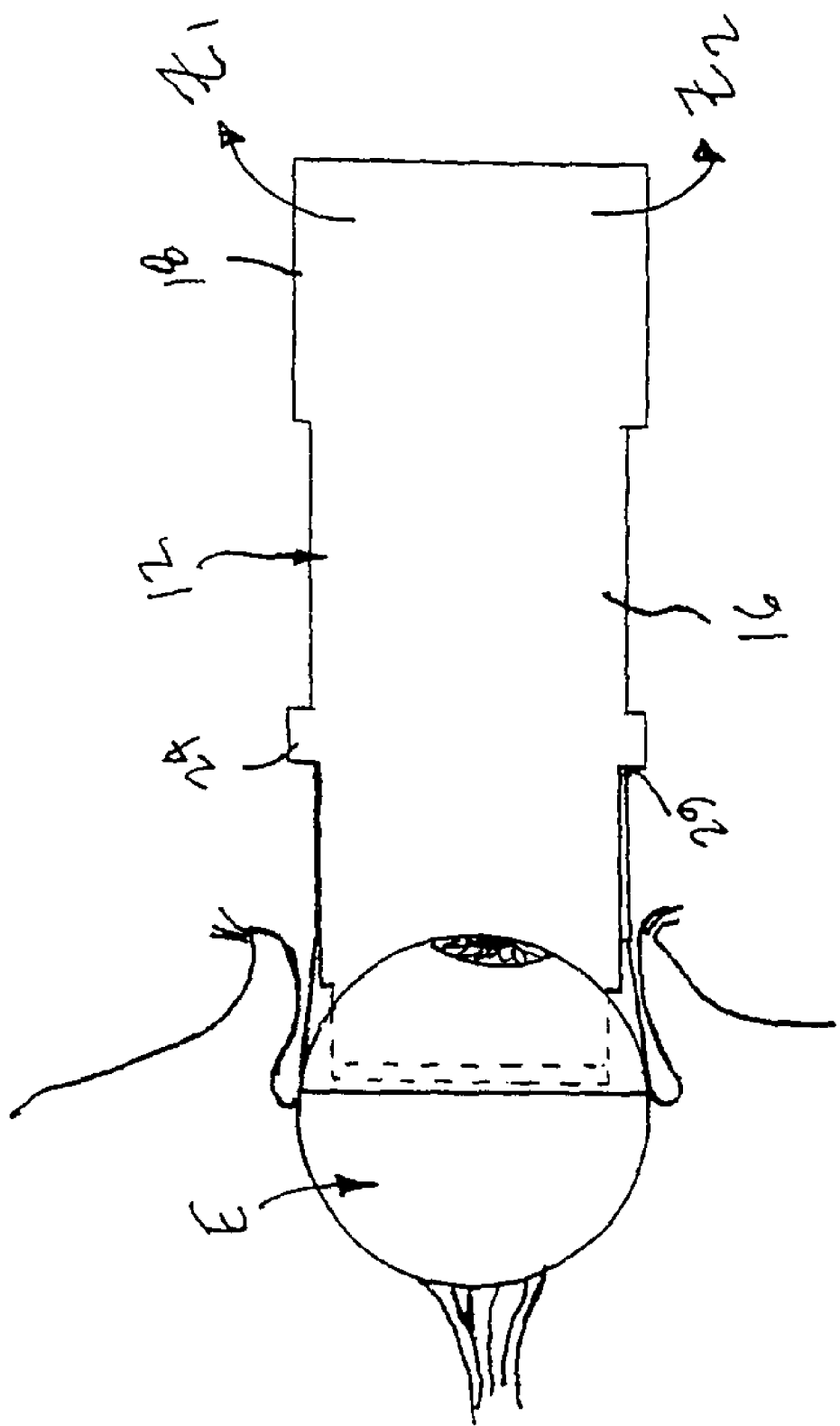
FIG. 5 is a sectional view along the line X-X of FIG. 1.

After insertion of the stabilizing portion 14 into the eye E, the user begins insertion of the cutting portion 12 into the stabilizing portion 14 in the direction of the action arrow A in FIG. 4. The user continues to insert the cutting portion 12 into the stabilizing portion 14 and the eye E until the rim 24 of the cutting portion 12 engages the top surface 29 of the stabilizing portion 14 (FIG. 5). As previously mentioned, the rim 24 functions as a stop to the limit the distance the cutter 20 may be inserted into the eye. Once fully inserted, the user may freely rotate the cutting portion 12 in the direction $Z_1$ and/or $Z_2$ (FIG. 5). After the desired cut has been made, the user may remove the cutting portion 12 from the eye E and stabilizing portion 14 by pulling the cutting portion in the direction of the action arrow B in FIG. 4. At this point, the user may remove the transplant material by simply lifting it from the eye E. One will appreciate that the present configuration of the stabilizing portion 14 and cutting portion 12 enables a user to accurately remove cornea material, as well as a portion of the sclera region of the eye, if desired. After the transplant material has been removed, the user may remove the stabilizing portion from the eye E.

Figure 9:
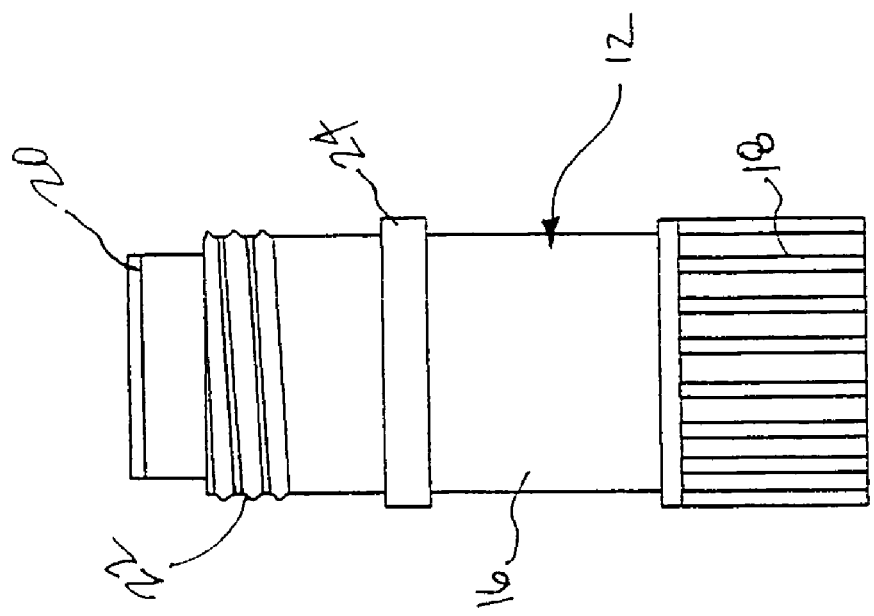
FIG. 9 is a side view of one possible embodiment of a cutting portion of the device of FIG. 7.

In another embodiment shown in FIGS. 7-13d, the cutting portion 12 includes threads 22 positioned adjacent the cutter 20 (see FIG. 9). The threads 22 are adapted to engage matching threads 36 (FIGS. 13a-13d) positioned on the inside of the stabilizing portion 14. This embodiment of the cutting portion 12 also includes the projection or rim 24 positioned between the threads 22 and gripping portion 18. As discussed below in further detail, the rim 24 engages a recess 26 (FIGS. 13a-13d) of the stabilizing portion 14, therein functioning as a stop to limit the distance the cutter 20 may extend beyond the stabilizing portion 14.

Figure 8:
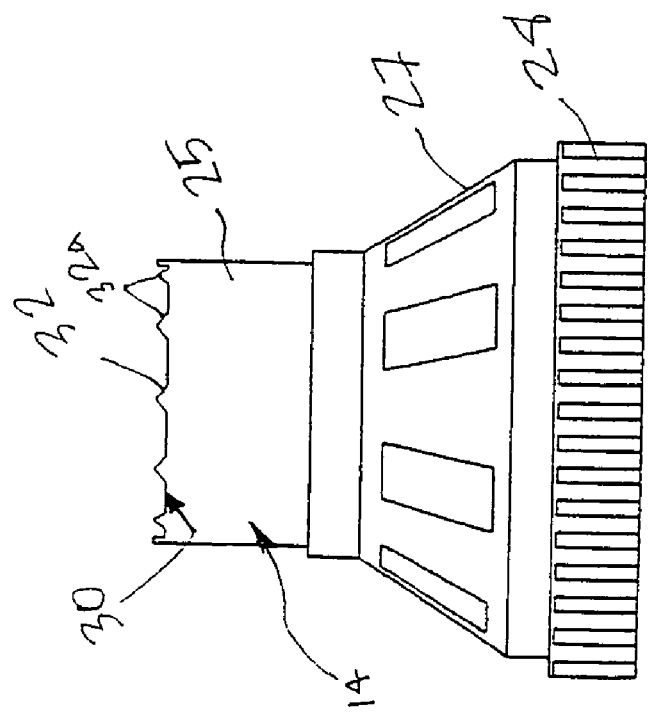
FIG. 8 is a side view of one possible embodiment of a stabilizing portion of the device of FIG. 7.
Figure 10:
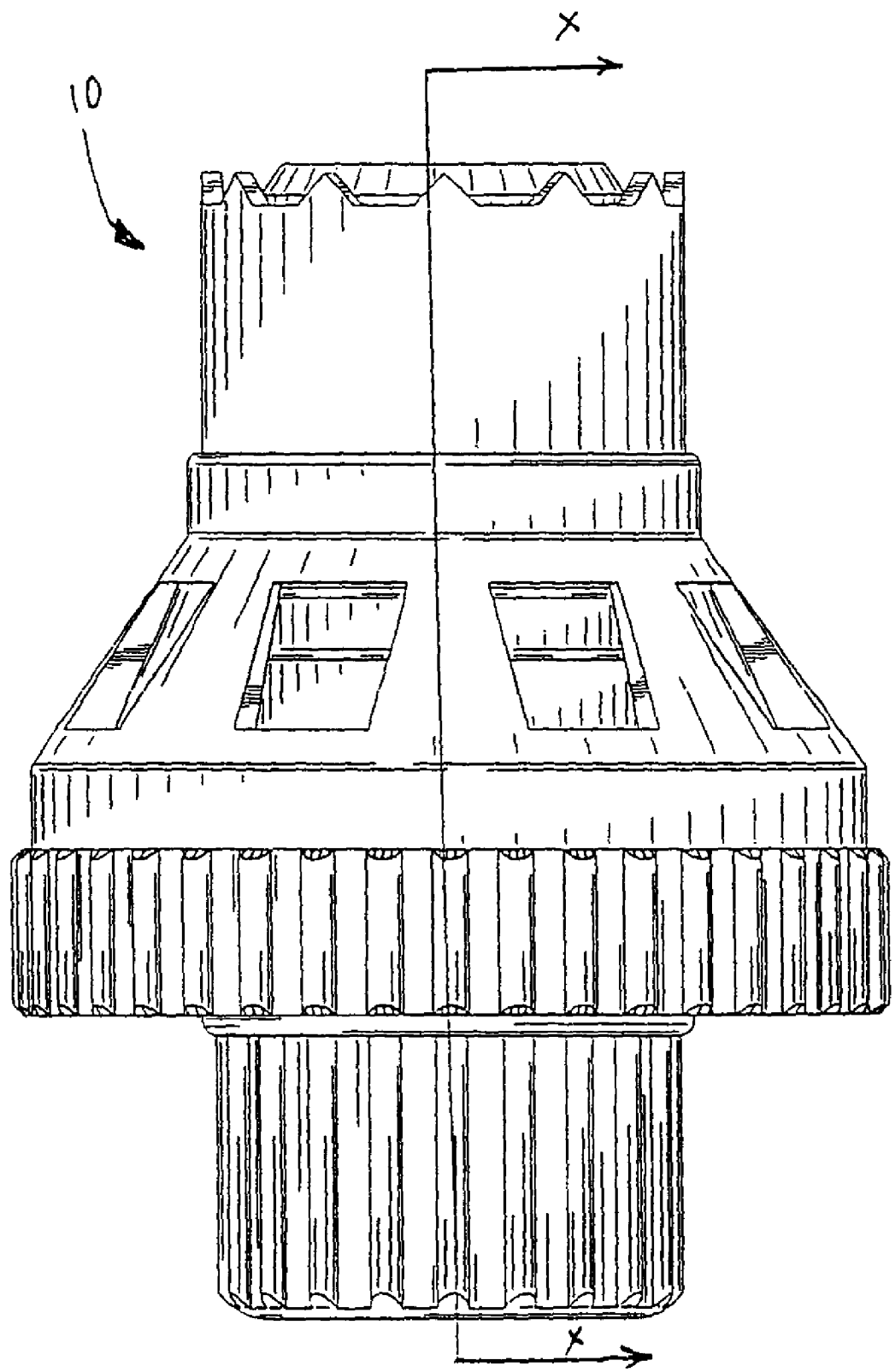
FIG. 10 is a side view of the device of FIG. 7.
Figure 11:
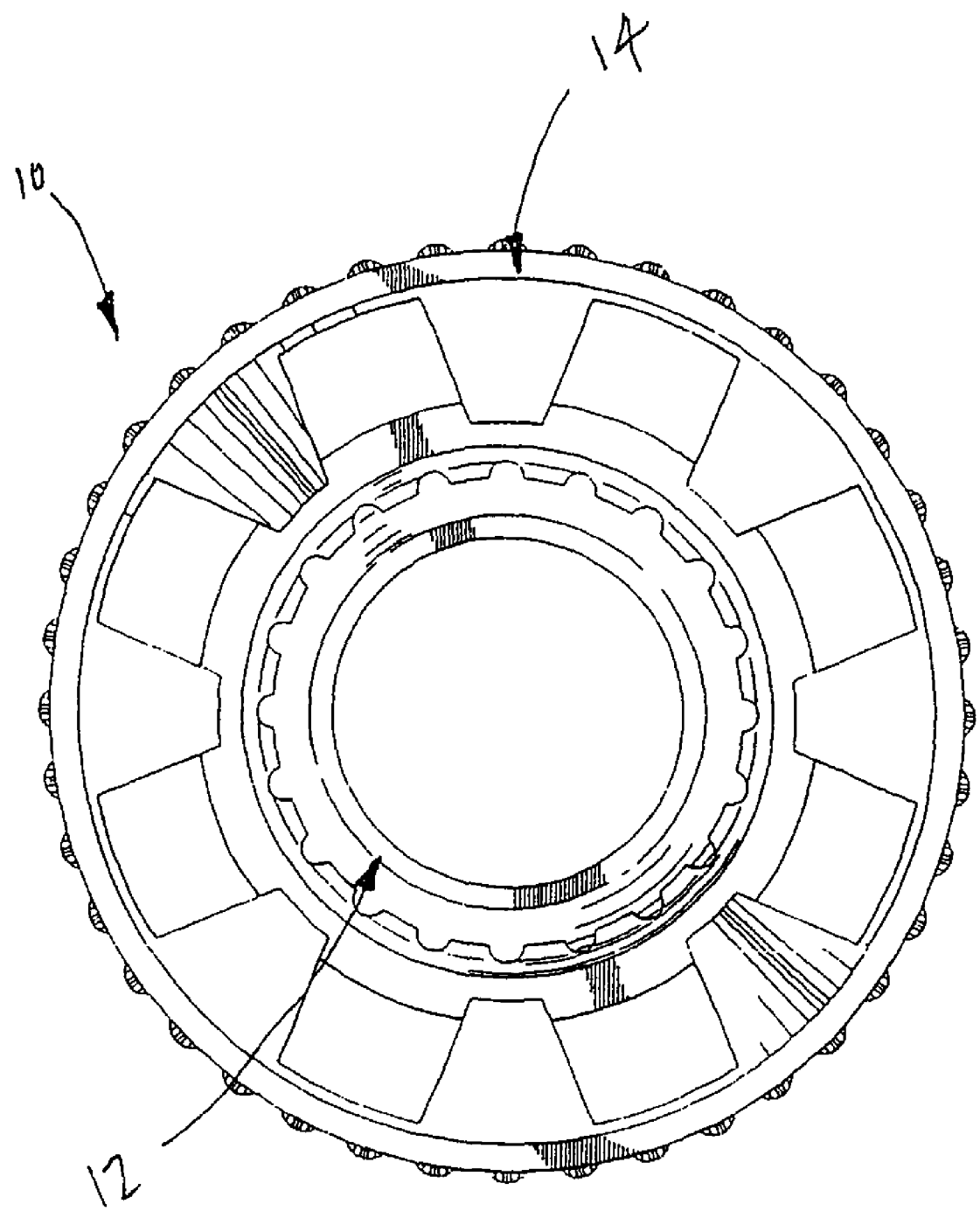
FIG. 11 is a bottom view of the device of FIG. 7.
Figure 12:
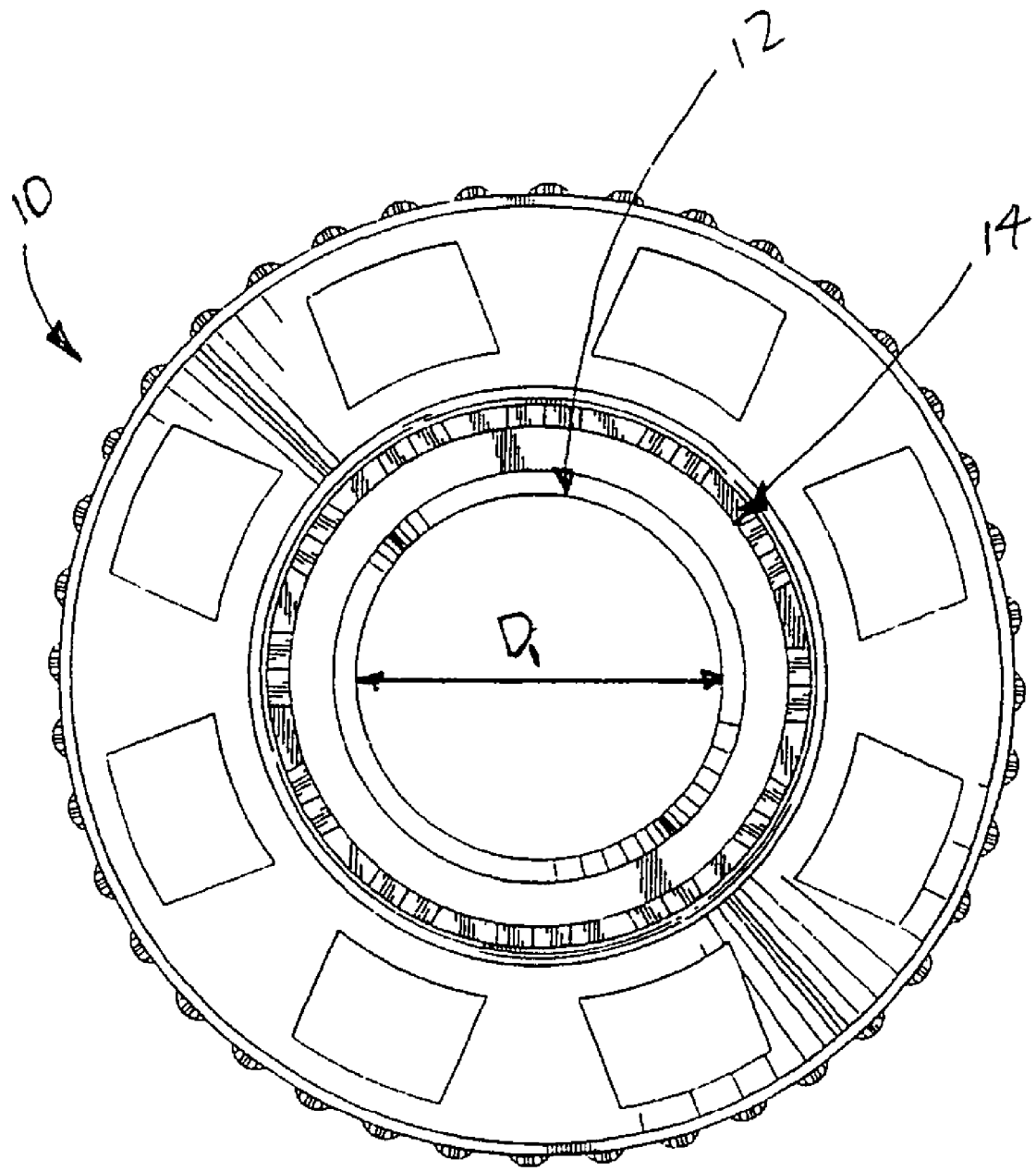
FIG. 12 is a top view of the device of FIG. 7.
Figure 13B:
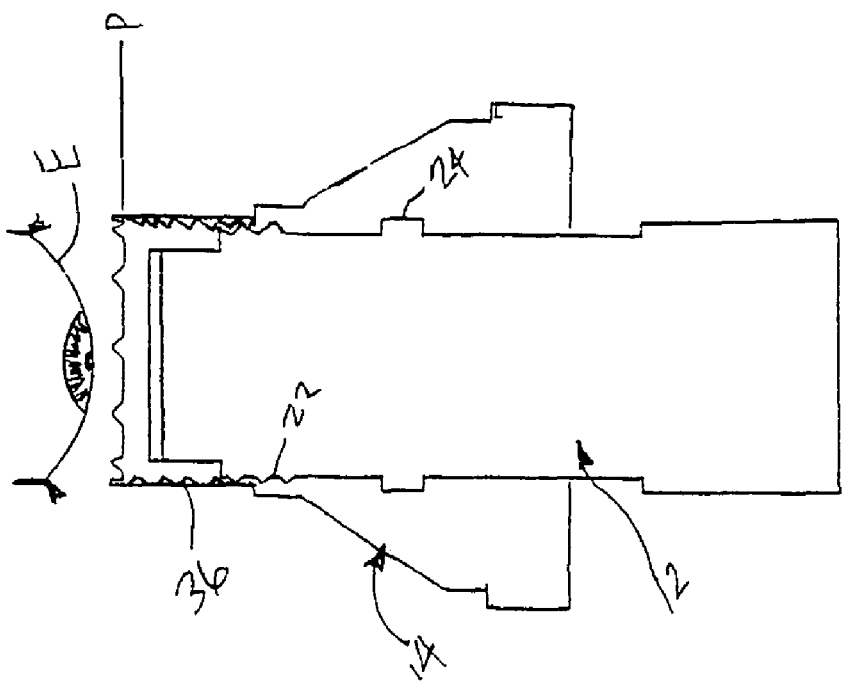
FIGS. 13b-13d are sectional views along the line X1-X1 of FIG. 10 showing one embodiment of a method of using the device of FIG. 7.
Figure 13A:
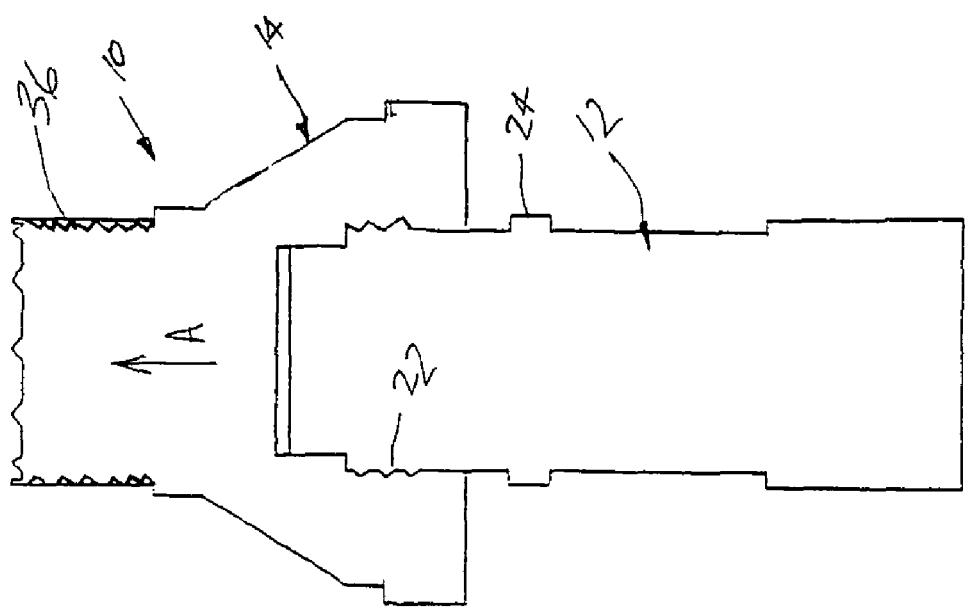
FIG. 13a is a sectional view along the line X1-X1 of FIG. 10 showing one embodiment of assembly of the device of FIG. 7.
Figure 13D:
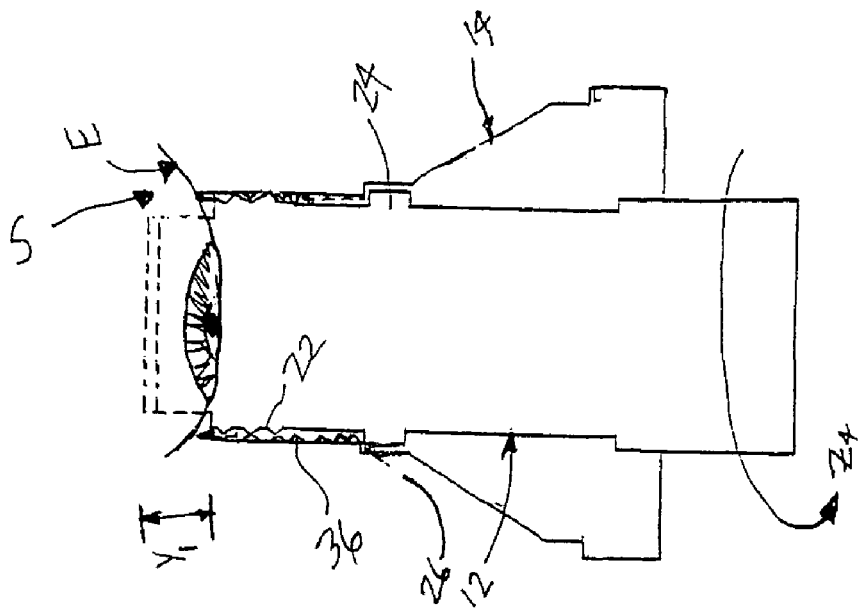
Figure 13C:
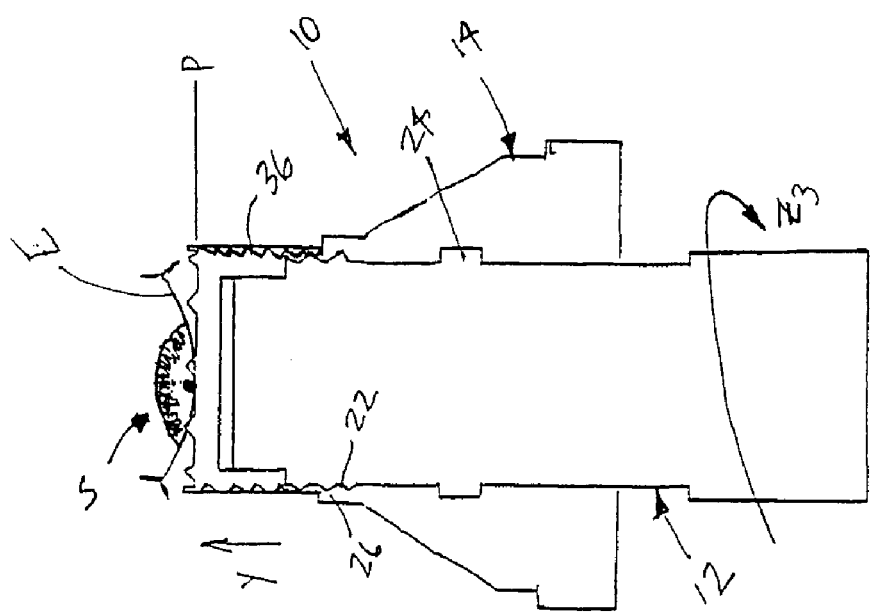

With specific reference to FIG. 8, the stabilizing portion 14 may include a substantially cylindrical region or tube 25 having a stabilizer 30 and a flared region 27 having a second gripping portion 28. As shown, the stabilizer 30 includes a serrated edge 32 formed from a plurality of teeth 32a. In one embodiment, the serrated edge 32 includes twelve teeth equally spaced about the circumference of the tube 25 for engagement with an eye E (FIGS. 13c and 13d). The stabilizer 30 functions to prevent movement of the stabilizing portion during the process of obtaining transplant material. Although shown with a flared portion 34, the stabilizing portion 14 may have any diameter that enables insertion of the cutting portion 12.

To assemble and use this embodiment of the device 10, the user inserts the cutting portion 12 into the stabilizing portion 14. With reference to FIG. 13b, the threads 22 of the cutting portion 12 engage the threads 36 of the stabilizing portion 14 in a standard screw arrangement. At this point, the device 10 is ready for engagement with the eye E.

One will appreciate that, prior to engagement with the eye E, the cutter 20 does not extend beyond a plane P defined by the serrated edge 32 (FIG. 13b). Since the tube 16 of the cutting portion 12 and the tube 25 of the stabilizing portion 14 are substantially hollow, the user of the device may accurately align the device 10 on the eye E by sighting through the device 10.

As shown in FIG. 13c, the user places the device 10 such that the serrated edge 32 engages the eye E and prevents undesired rotation of the stabilizing portion 14 during the excision process. Unlike the previous embodiment where the stabilizing portion 14 became inserted in the eye E, the present embodiment only rests on the sclera S of the eye E. Once positioned, the user may begin turning the cutting portion 12 to cut the eye E. As shown in FIG. 13c, the cutting portion 12 is turned in a direction $Z_3$ such that is proceeds in a direction Y along the threads 36 of the stabilizing portion 14.

The cutter 20 continues to cut until the rim 24 engages the recess 26 (FIG. 13d). A skilled artisan will appreciate that the engagement of the rim 24 in the recess 26 prevents any further cutting beyond a desired point. This ensures that the user does not make a cut that is too deep or not deep enough.

In other embodiments, the cutting portion 12 may also include a flared region 27'. As shown in FIG. 14, one end of the cutting portion 12 includes the flared region 27', while the other end includes the cutter 20. The flared region 27' on the cutting portion 12 provides a larger gripping surface for the user of the device 10, as well as greater visibility of the eye E when aligning the device 10. Similar to the previous embodiments, the stabilizing portion 14 with the flared region 27' may also include a stop 37 for limiting the distance the cutter 20 may extend beyond the plane P'. Alternatively, a shoulder 39 of the flared region 27' may function to limit the cutting distance. Specifically, the shoulder 39 may engage a surface, such as the top surface 41, of the stabilizing portion 14 when inserted, therein limiting the distance the cutter 20 may extend and obviating the need for the stop 37. Although shown in FIG. 14 as including the substantially cylindrical tube 16 between the flared region 27' and the cutter 20, the flared region 27' may terminate with the cutter 20, thereby eliminating the need for the cylindrical tube 16.

In any of the embodiments shown in FIG. 14, the cutting portion 12 becomes inserted into the stabilizing portion 14 in the direction A'. As with the previously discussed embodiment, the threads 22 of the cutting portion 12 engage the threads of the stabilizing portion 14. Prior to engagement with the eye E, the cutter 20 does not extend beyond a plane P' defined by the edge 31 of the stabilizer 30.

Similar to the recess 26 in the previous embodiment, the stabilizing portion 14 may also include a stop 37, such as a projection or recess for limiting the distance the cutter may extend beyond the plane P'. As the cutting portion 12 becomes inserted in the stabilizing portion 14, the rim 24 engages the stop 37, therein functioning to limit the distance the cutter 20 may extend beyond the plane P'. Depending on the desired depth of cut, this stop 37 may be positioned at any point along the interior of the tube 25. The stop 37 may also be positioned in the flared region 27, if desired.

Identical to the operation of the device 10 as previously discussed, the user aligns the device 10 on the eye E by sighting through the substantially hollow tube 16 of the cutting portion 12 and the tube 25 of the stabilizing portion 14. As previously discussed, positioning the stabilizer 30 at the flared region 27 enables the user to insert the device into the eye E, such that the flared region 27 encircles a portion of the eye E. This causes a portion of the stabilizer 30 to engage the conjunctival fornix C.

In any of the embodiments, the device 10 may be configured for any cutting distance. Preferably, the cutter 20 is configured to extend a distance $Y_1$ of 0.1-1.4 mm into the eye E (FIGS. 13c and 13d). Upon completion of the single cut, the cutter 20 may become disconnected from the eye E by rotating the cutting region 12 in a direction $Z_4$, opposite from the direction $Z_3$ (FIGS. 13c and 13d). At this point, the device 10 may be removed from the eye E and the transplant material may simply be lifted from the eye E. One will appreciate that the device 10 may obtain transplant material including the cornea, as well as 2-4 mm of the sclera region of the eye. In the event that the donor's eye socket is too small to receive the stabilizing portion 14, the user may extend the cutter 20 and score the area of the cornea to be removed via scissors or other surgical tools.

The foregoing descriptions of various embodiments of the invention are provided for purposes of illustration, and are not intended to be exhaustive or limiting. Modifications or variations are also possible in light of the above teachings. For example, the device 10 may include an auxiliary handle for further control of the device. In addition to obtaining transplant material, the device 10 may be modified dimensionally or otherwise for use in the eye of the recipient of the transplant material and/or for obtaining the button to be transplanted. Also, in any of the embodiments, the cutter 20 may be a separate piece from the cutting portion 12. Thus, the cutter 20 may be inserted and removed from the cutting portion 12, as desired. Alternatively, the cutter 20 may comprise a semi-permanent attachment to the cutting portion via friction fit, brazing, welding or otherwise. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. A device for cutting or scoring the eye, comprising:
   a cutting portion having an annular cutter and a projection spaced apart from the cutter, the cutting portion becomes inserted into a stabilizing portion to cut or score the eye;
   the stabilizing portion comprising a single member having both an interior with a stop and a serrated edge formed from a plurality of teeth;
   wherein the cutting portion is movable with respect to the stabilizing portion, and upon inserting the stabilizing portion in the eye, the serrated edge rests on the eye, and the projection may engage the stop to limit the distance the cutting portion may be inserted in the eye, wherein the cutting portion and the single member of the stabilizing portion each have matching threads.

2. The corneal excision or scoring device of claim 1, wherein the stabilizing portion and the cutting portion are substantially hollow concentric tubes.

3. The corneal excision or scoring device of claim 2, wherein the projection comprises a substantially circular rim having a diameter greater than a diameter of the substantially hollow tube of the cutting portion.

4. The corneal excision or scoring device of claim 3, wherein the stop comprises a projection.

5. The corneal excision or scoring device of claim 3, wherein the stop comprises a recess.

6. The corneal excision or scoring device of claim 3, wherein the cutting portion and stabilizing portion each have matching threads, thereby enabling a user to mechanically join the cutting and stabilizing portions.

7. The corneal excision or scoring device of claim 6, wherein the substantially circular rim resides between the threads on the cutting portion and a gripping portion.

8. A device for cutting or scoring the eye, comprising:
   a cutting portion having a cutter following an entire perimeter of the cutting portion and a projection spaced apart from the cutter, the cutting portion becomes inserted into a stabilizing portion to cut or score the eye;
   the stabilizing portion comprising a single member having both an interior with a stop and a serrated edge formed from a plurality of teeth;
   wherein the cutting portion and the single member of the stabilizing portion each have matching threads for mechanically joining the cutting portion and the stabilizing portion, and the cutting portion is movable with respect to the stabilizing portion, and upon inserting the stabilizing portion in the eye, the serrated edge rests on the eye, and the stop limits the distance the cutting portion may be inserted.

9. The conical excision or scoring device of claim 8, wherein the cutting portion comprises a substantially cylindrical tube.

10. The corneal excision or scoring device of claim 9, wherein the projection comprises a rim having a diameter greater than a diameter of the cutting portion.

11. The corneal excision or scoring device of claim 8, wherein the cutting portion includes a gripping portion at one end and the cutter at the other.

12. The corneal excision or scoring device of claim 8, wherein the threads of the cutting portion are positioned between the cutter and the projection.

13. The corneal excision or scoring device of claim 8, wherein the stabilizing portion includes a plurality of apertures that enable a user to better visualize the alignment of the corneal excision or scoring device with the eye.

14. The corneal excision or scoring device of claim 8, wherein the stop comprises a recess that receives the projection.

15. The corneal excision or scoring device of claim 8, wherein the stabilizing portion includes a flared region having a plurality of apertures.

16. A device capable of resting on the sclera of an eye and cutting or scoring the eye, comprising:
   a cutting portion comprising a substantially cylindrical tube having a gripping portion at one end and a cutter at the other end, the cutter comprising an uninterrupted blade substantially following an entire perimeter of the tube;
   a stabilizing portion comprising a single member having both an interior with a recess and a serrated edge formed from a plurality of teeth, the cutting portion becomes inserted into a stabilizing portion to cut or score the eye;
   wherein the cutting portion and the single member of the stabilizing portion each have matching threads for mechanically joining the cutting portion and the stabilizing portion, and the cutting portion is movable with respect to the stabilizing portion, and upon inserting the stabilizing portion in the eye, the serrated edge rests on the eye, and the recess limits the distance the cutting portion may be inserted.

17. The corneal excision or scoring device of claim 16, wherein the threads of the cutting portion are positioned between the cutter and a projection.

18. The corneal excision or scoring device of claim 17, wherein the threads of the stabilizing portion are positioned between the recess and the serrated edge.

19. The corneal excision or scoring device of claim 16, wherein the stabilizing portion includes a first region having a first diameter and a second region having a second diameter, the second diameter is larger than the first diameter, and the first region including the serrated edge and the second region including a plurality of apertures.

20. The corneal excision or scoring device of claim 16, wherein the stabilizing portion includes a flared region having a plurality of apertures.

* * * * *

UNITED STATES PATENT AND TRADEMARK OFFICE
CERTIFICATE OF CORRECTION

PATENT NO. : 7,744,614 B2 Page 1 of 1
APPLICATION NO. : 11/452017
DATED : June 29, 2010
INVENTOR(S) : Gayheart et al.

It is certified that error appears in the above-identified patent and that said Letters Patent is hereby corrected as shown below:

Claim 9, column 8, line 26, please replace "conical" with -- corneal --.

Signed and Sealed this

Thirty-first Day of August, 2010

David J. Kappos
*Director of the United States Patent and Trademark Office*